(12) United States Patent
Bi et al.

(10) Patent No.: US 10,288,814 B2
(45) Date of Patent: May 14, 2019

(54) VARIABLE SPATIAL OFFSET FIBER OPTIC PROBE FOR OPTICAL SPECTOGRAPHY AND IMAGING

(71) Applicant: BOARD OF REGENTS OF THE UNIVERSITY OF TEXAS SYSTEM, Austin, TX (US)

(72) Inventors: Xiaohong Bi, Pearland, TX (US); Zhiyong Wang, Sugar Land, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 302 days.

(21) Appl. No.: 15/080,256

(22) Filed: Mar. 24, 2016

(65) Prior Publication Data

US 2016/0282273 A1    Sep. 29, 2016

Related U.S. Application Data

(60) Provisional application No. 62/137,926, filed on Mar. 25, 2015.

(51) Int. Cl.
| | |
|---|---|
| *G02B 6/35* | (2006.01) |
| *G01N 21/49* | (2006.01) |
| *G01N 21/65* | (2006.01) |
| *A61B 5/00* | (2006.01) |
| *G02B 6/00* | (2006.01) |

(52) U.S. Cl.
CPC .......... *G02B 6/3504* (2013.01); *A61B 5/0075* (2013.01); *G01N 21/49* (2013.01); *G01N 21/65* (2013.01); *G02B 6/00* (2013.01); *G02B 6/3578* (2013.01); *A61B 5/4504* (2013.01); *A61B 2562/0233* (2013.01); *G01N 2201/0846* (2013.01)

(58) Field of Classification Search
CPC .... G02B 6/3504; G02B 6/3578; G01N 21/49; G01N 21/65; G01N 2201/0846; A61B 5/0075; A61B 2562/0233; A61B 5/4504
See application file for complete search history.

(56) References Cited

U.S. PATENT DOCUMENTS

| | | | |
|---|---|---|---|
| 7,652,763 | B2 | 1/2010 | Matousek et al. |
| 7,911,604 | B2 | 3/2011 | Matousek et al. |
| 8,259,902 | B2 | 9/2012 | Matousek et al. |
| 9,020,581 | B2 | 4/2015 | Mahadevan-Jansen et al. |
| 9,289,130 | B2 | 3/2016 | Mahadevan-Jansen et al. |
| 2010/0145200 | A1 | 6/2010 | Mahadevan-Jansen et al. |
| 2011/0306956 | A1* | 12/2011 | Islam ............... A61B 18/20 606/15 |
| 2012/0232821 | A1* | 9/2012 | Liu ................. A61B 5/0066 702/77 |
| 2014/0140594 | A1 | 5/2014 | Mahadevan-Jansen et al. |

* cited by examiner

*Primary Examiner* — Ryan A Lepisto
(74) *Attorney, Agent, or Firm* — Blank Rome LLP (57) ABSTRACT

Apparatus and method for optical spectroscopy and/or imaging with a variable fiber offset. An optical probe includes one or more first optical fibers, one or more second optical fibers, and one or more actuators. The first optical fibers are to deliver light to an object. The second optical fibers are to collect light emitted from the object. The actuators are configured to change a distance between the first optical fibers and the second optical fiber while the object is being illuminated by light emitted from the first optical fibers.

10 Claims, 13 Drawing Sheets

VARIABLE SPATIAL OFFSET FIBER OPTIC PROBE FOR OPTICAL SPECTOGRAPHY AND IMAGING

CROSS REFERENCE TO RELATED APPLICATIONS

This application is a non-provisional application claiming priority to provisional application Ser. No. 62/137,926, filed on Mar. 25, 2015, entitled "Variable Spatial Offset Probe for Optical Spectrography and Imaging," the entire disclosure of which is incorporated by reference herein.

STATEMENT REGARDING FEDERALLY SPONSORED RESEARCH OR DEVELOPMENT

This invention was made with U.S. Government support under K25CA149194-01 awarded by the National Institutes of Health. The government has certain rights in the invention.

BACKGROUND

Light-scattering and light-absorption based optical spectroscopy and imaging are powerful analytical and detection tools that have applied in pharmaceutical, material, chemical, biomedical, and a wide variety of other applications. The scattering and absorption processes occurring between light and matter can be elastic (e.g. Rayleigh scattering, infrared absorption, etc.) or inelastic (e.g. fluorescence scattering, Raman scattering, etc.). In an elastic process, the energy (i.e. the wavelength) of the incident photon is conserved to render the scattered photon with an identical wavelength, and only the direction of the scattered photon is changed. In an inelastic process, the incident photon interacts with matter and the frequency of the scattered photon is shifted to red or blue. A red shift occurs when part of the energy of the incident photon is transferred to the interacting matter, whilst the blue shift occurs when internal energy of the matter is transferred to the incident photon. Absorption occurs when the entire energy of the incident photon is transferred to the interacting matter and the photon annihilates.

Raman spectroscopy is an optical spectroscopic technique based on inelastic scattering of monochromatic light that can provide molecular information for specimens via probing vibrational energy transitions in molecules. In the Raman scattering process, molecules scatter photons, altering the photons' energy with energy quanta that are equivalent to the molecules' vibrational eigen-energies. Thus, Raman spectroscopy detects molecular vibrations of specimens. Raman spectroscopy can potentially be employed for in vitro and in vivo diagnosis of diseases and malignancies, in various tissues (e.g. lung, breast, prostate, ovarian, brain, bone and etc.), originating from biochemical differences between normal and diseased/malignant tissues. Because Ramen spectroscopy can provide information about molecular structure and composition of specimens with no contrast agents, Raman spectroscopy offers valuable complimentary information to current anatomical or functional imaging techniques such as electrochemical, electrical, thermal, ultrasound, X-ray and nuclear magnetic resonance (NMR).

BRIEF DESCRIPTION OF THE DRAWINGS

For a detailed description of exemplary embodiments of the invention, reference will now be made to the accompanying drawings.

NOTATION AND NOMENCLATURE

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including," "includes," "comprising," and "comprises" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections. The recitation "based on" is intended to mean "based at least in part on." Therefore, if X is based on Y, X may be based on Y and any number of other factors.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Use of traditional Raman techniques have been restricted by shallow penetration depth, which is typically less than one millimeter. This limitation renders many tissue components, such as deep cancerous tissues and bones, inaccessible by traditional Raman techniques. The development of spatially offset Raman spectroscopy (SORS) has increased penetration depth using diffuse optical techniques. SORS can detect Raman signals at a penetration depth up to several millimeters and in some cases several centimeters. Moreover, SORS can achieve differentiation of Raman signals in terms of depths inside the sample, and has been investigated for use in detection of bone diseases, cancers, glucose levels, and pharmaceuticals.

Conventional SORS fiber optic probes generally include a limited amount of fibers that are fixed in place. Such an arrangement offers constant offsets ($\Delta$s) between excitation and collection units. If a large range of $\Delta$s is necessary (e.g. for large or deep samples), the fiber probe must include more collection fibers or multiple channels of illumination/collection units, which is not cost efficient and provides little flexibility for interrogating samples at different depth. Furthermore, when multiple collection units are utilized in SORS, each fiber requires individual calibration for system and background correction. Thus, more fibers lead to more complicated calibration and operational procedures.

Embodiments of the present disclosure include a novel probe for SORS and other optical spectroscopy and imaging. The probe includes actuators (e.g., a mechanical iris) and offers adjustable distances between collection and excitation fibers. The fiber probe disclosed herein provides a cost-effective solution for various Raman applications. Embodiments of the probe include optical fibers (or fiber bundles), motorizing mechanisms and miniaturized optics. The optical fibers (or fiber bundles) deliver excitation lasers to specimens and collect emitted optical signals from specimens. The motorizing mechanisms (e.g. microelectromechanical systems (MEMS), piezoelectric (e.g. lead zirconate titanate (PZT)) or mechanical actuators (e.g. a mechanical iris with an open "eye")) are applied to fine tune the distances, $\Delta$s, between the excitation and collection fibers (or fiber bundles) in order to obtain emitted optical signals from different depths within specimens. The spatial offsets between the excitation and collection fibers (or fiber bundles) lead to corresponding spatial offsets between the excitation and collection regions on specimens. The miniaturized optics manipulate the light paths of lasers and optical signals, to optimize their excitation and collection efficiencies and to optically filter out unwanted wavelengths. The molecular information obtained from emitted spectroscopic spectra can be used for analyzing deep layers of samples of interest such as various turbid tissues (e.g. bone, lung, breast, prostate, ovarian, brain, bladder, colon, larynx, cervix, skin and etc.) and/or differentiating normal tissues, malignant tissues and benign tissues.

Figure 1:
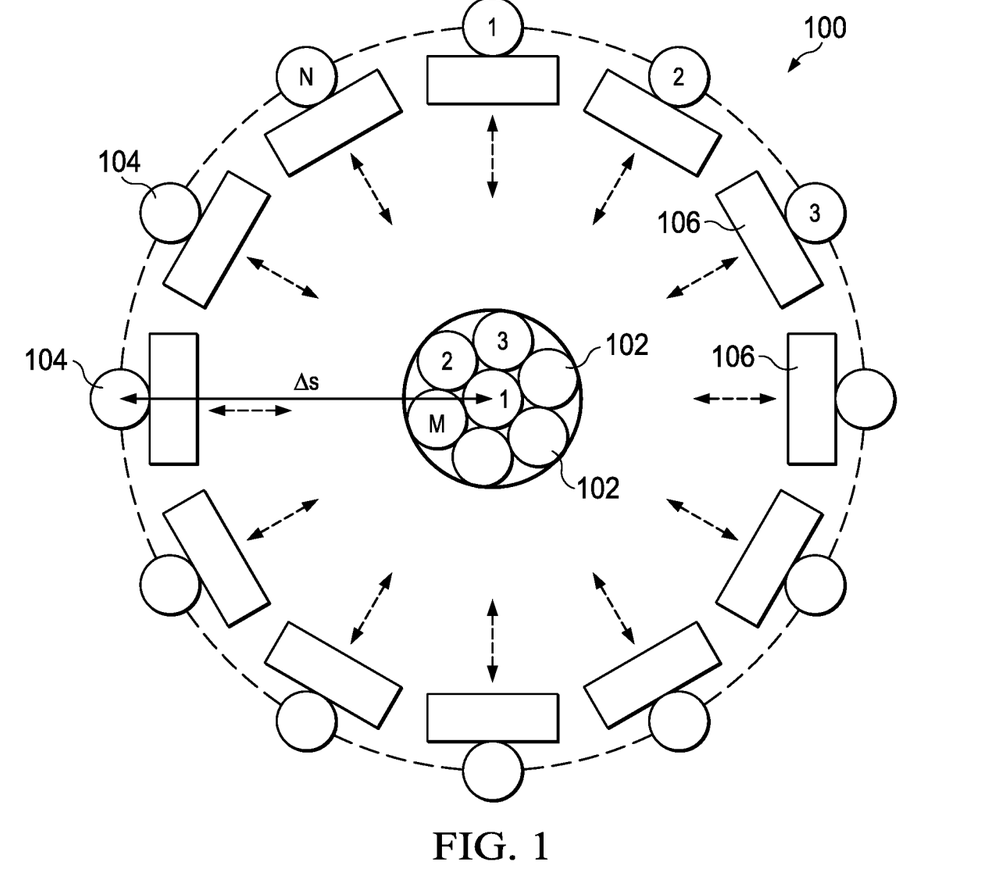
FIGS. 1-8 shows schematic illustrations of views of various embodiments of a fiber optic probe that provides variable distance between excitation and collection fibers in accordance with principles disclosed herein.

FIG. 1 shows a schematic diagram of fiber optic probe 100 in accordance with principles disclosed herein. The probe 100 includes optical fibers (or fiber bundles) 102 and 104, motorized actuators 106, and miniaturized optics (e.g. collimating lenses, GRIN lenses, or optical filters). The miniaturized optics have been omitted from FIG. 1 in the interest of clarity. The probe 100 includes two sets of optical fibers (or fiber bundles) 102 and 104. The optical fiber(s) (or fiber bundle(s)) 102 are positioned at the center of the probe 100. The optical fibers (or fiber bundles) 104 are separately mounted on individual motorized actuators 106 surrounding the central fibers 102. The central fibers 102 may be one or more single-mode/multimode fibers. Similarly, the fibers 104 mounted on the actuators 106 may be one or more single-mode/multimode fibers. The fibers 102 and 104 may serve as excitation fibers and collection fibers respectively or versus versa for optical spectroscopy and/or imaging applications.

The motorized actuators 106 may be microelectromechanical systems (MEMS) actuators, piezoelectric (e.g. lead zirconate titanate (PZT)), or other types of mechanical actuators. The motorized actuators 106 are applied to tune the spatial offsets, $\Delta$s, between the excitation and collection fibers by moving the surrounding fibers 104 closer to or farther away from the central fibers 102 to obtain optical signals from different depths within specimens or objects being imaged. The spatial offsets between the excitation and collection fibers lead to corresponding spatial offsets between the excitation and collection regions on specimens (e.g., specimen surface). The actuators 106 may be arranged as a ring structure with a certain initial radius. Tuning of spatial offsets, $\Delta$s, may be provided by increasing or decreasing the radius of the ring using the motorized actuators. In some embodiments, use of the actuators 106 to change the distance between the fibers 102 and the fibers 104, provides an ability to obtain readings through translucent containers/structures of varying thicknesses and other physical properties.

Figure 2:
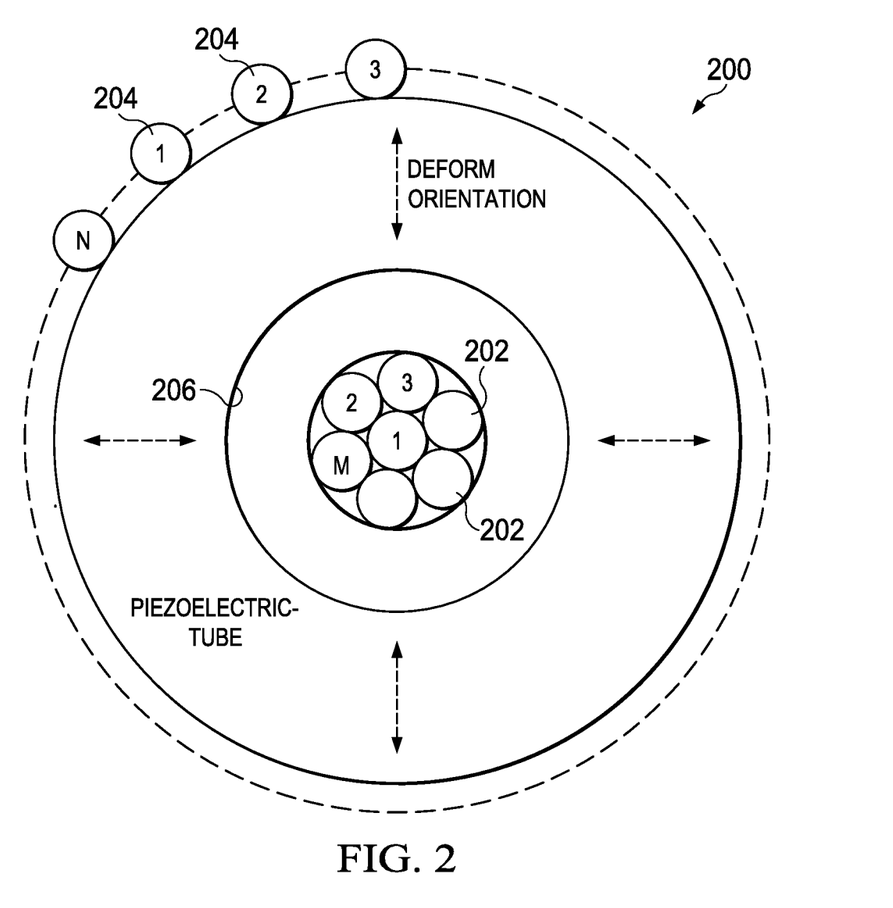

FIG. 2 shows a fiber optic probe 200 in accordance with principles disclosed herein. The probe 200 includes optical fibers (or fiber bundles) 202 and 204, piezoelectric-tube actuators 206, and miniaturized optics (e.g. collimating lenses, GRIN lenses, or optical filters). The miniaturized optics have been omitted from FIG. 2 in the interest of clarity. The optical fibers 202, 204 are similar to the optical fibers 102, 104 described above with regard to the probe 100. Rather than discrete actuators, as included in the probe 100, the probe 200 includes one or more piezoelectric-tube actuators 206 that provide fine-tuning of the spatial offsets, $\Delta$s, between the excitation and collection fibers to obtain optical signals from different depths within specimens. A change of voltage applied across the piezoelectric-tube actuators 206 causes a change in distance between the optical fibers 202 and the optical fibers 204. The fibers 204 may be mounted on either the inner surface of the tube 206 or the outer surface of the piezoelectric tube 206.

Figure 3:
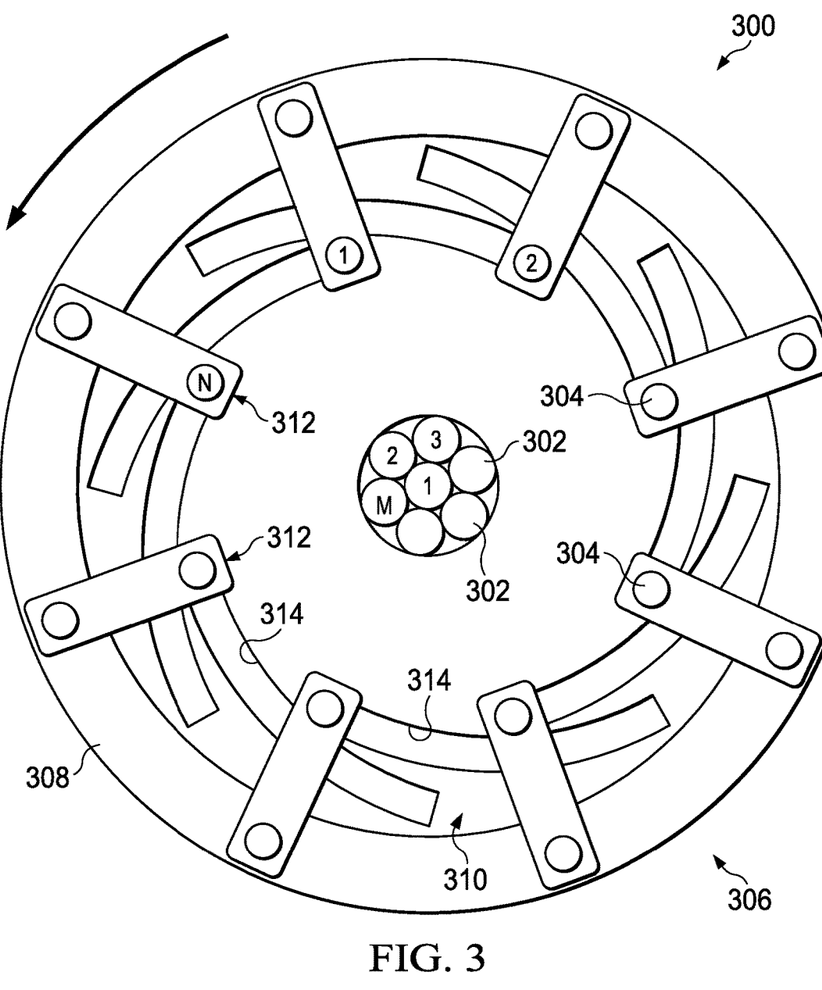

FIG. 3 shows a fiber optic probe 300 in accordance with principles disclosed herein. The probe 300 includes optical fibers (or fiber bundles) 302 and 304, a motorized mechanical iris 306, and miniaturized optics (e.g. collimating lenses, GRIN lenses, or optical filters). The miniaturized optics have been omitted from FIG. 3 in the interest of clarity. The optical fibers 302, 304 are similar to the optical fibers 102, 104 described above with regard to the probe 100. The motorized mechanical iris 306 includes an actuating ring 308, a base ring 310, and a plurality of blades 312. The optical fibers 304 are mounted on an end of the blades 312 that is nearest the fibers 302, while the other end of each blade 302 is rotatably connected to the actuating ring 308. The base ring 310 includes slots 314 that restrict the movement and location of the optical fibers 304 (i.e., guide the optical fibers 304). The actuating ring 308 may be rotated. Rotation of the actuating ring 308 moves each of the optical fibers 304, within a corresponding slot 314, nearer or farther away from the optical fibers 302. Consequently, the spatial offsets, Δs, between the surrounding fibers 304 and the central fibers 302 can be changed, allowing acquisition of optical signals from different depths within specimens. The actuating ring 308 may be manually driven, or driven by computer or otherwise electrically-controlled via a motor or other device.

Figure 4:
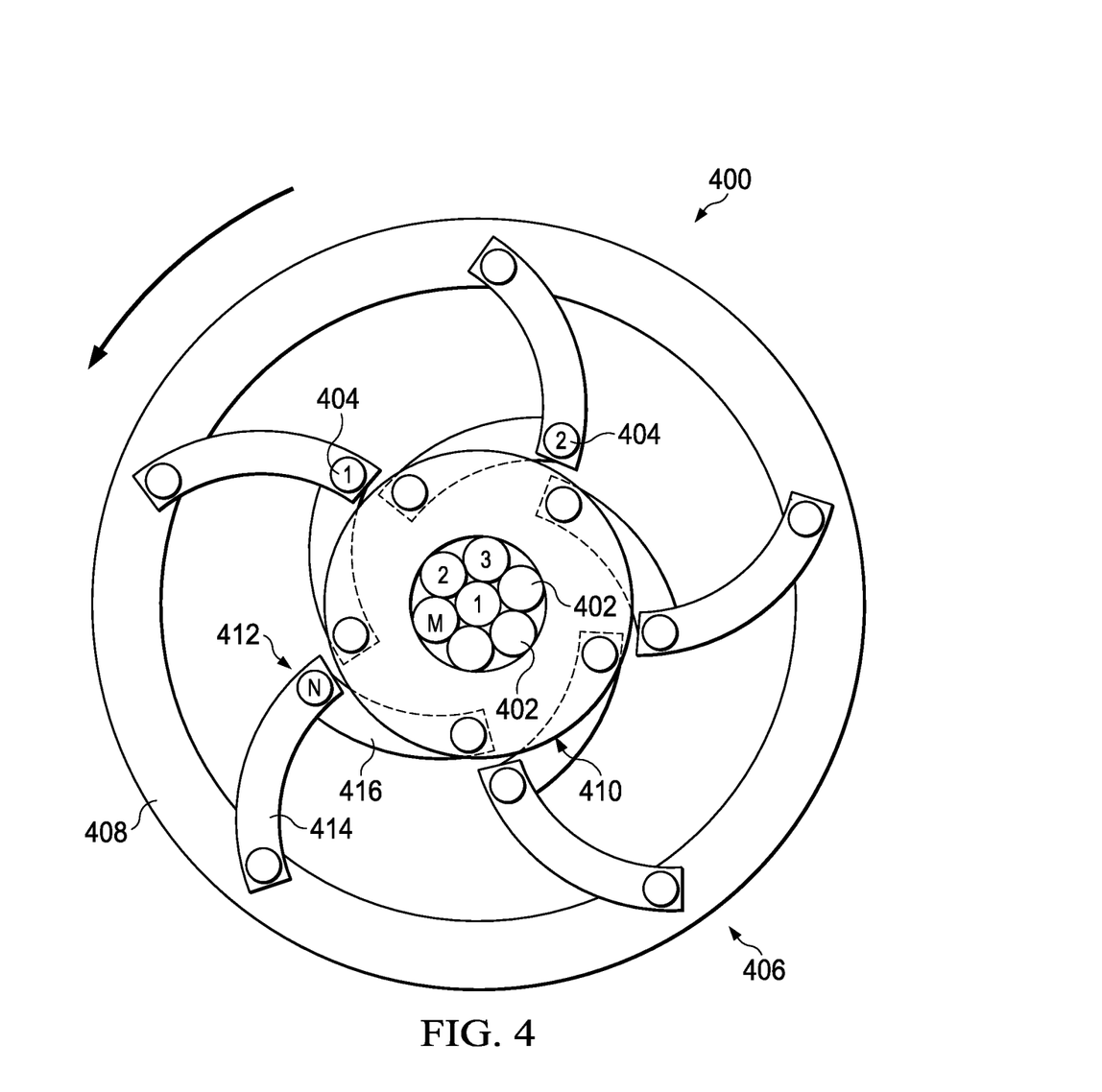

FIG. 4 shows a fiber optic probe 400 in accordance with principles disclosed herein. The probe 400 includes optical fibers (or fiber bundles) 402 and 404, a motorized mechanical iris 406, and miniaturized optics (e.g., collimating lenses, GRIN lenses, or optical filters). The miniaturized optics have been omitted from FIG. 4 in the interest of clarity. The optical fibers 402, 404 are similar to the optical fibers 102, 104 described above with regard to the probe 100. The motorized mechanical iris 406 includes an actuating ring 408, a base ring 410, and a plurality of blades 412. Each of the blades 412 includes an outer member 414 and an inner member 416. A first end of the outer member is rotatably connected to a first end of the inner member 416. A second end of the outer member 414 is rotatably connected to the actuating ring 408. A second end of the inner member 416 is rotatably connected to the base ring 410. The optical fibers 304 are mounted on the blades 412 at or near the connection/intersection of the outer member 414 and the inner member 416. The actuating ring 408 may be rotated. Rotation of the actuating ring 408 moves each of the optical fibers 404 nearer to or farther away from the optical fibers 402. Consequently, the spatial offsets, Δs, between the surrounding fibers 404 and central fibers 402 can be changed, allowing acquisition of optical signals from different depths within specimens. The actuating ring 408 may be manually driven, or driven by computer or otherwise electrically-controlled via a motor or other device.

FIGS. 5-8 show schematic illustrations of views of a fiber optic probe 500 in accordance with principles disclosed herein. The fiber optic probe 500 includes an iris 506, a turnkey 516, a set of turning rods 518, a set of frame support rods 520, an excitation fiber tube 502, and a plurality of collection fiber tubes 504. The excitation fiber tube 502 is fixed at the center of the iris 506. The iris 506 is similar to the iris 306, and includes moveable blades 512, actuating ring 508, and base ring 510, which includes arcuate slots 514. The collection fiber tubes 504 are mounted on the movable blades 512. The set of frame support rods 520 form a structure to support the turnkey 516 and the iris 506. The turning rods 518 are disposed between the frame support rods 520 and are used to rotate the iris 506 (i.e., rotate the actuating ring 508) in response to rotation of the turnkey 516.

Figure 5:
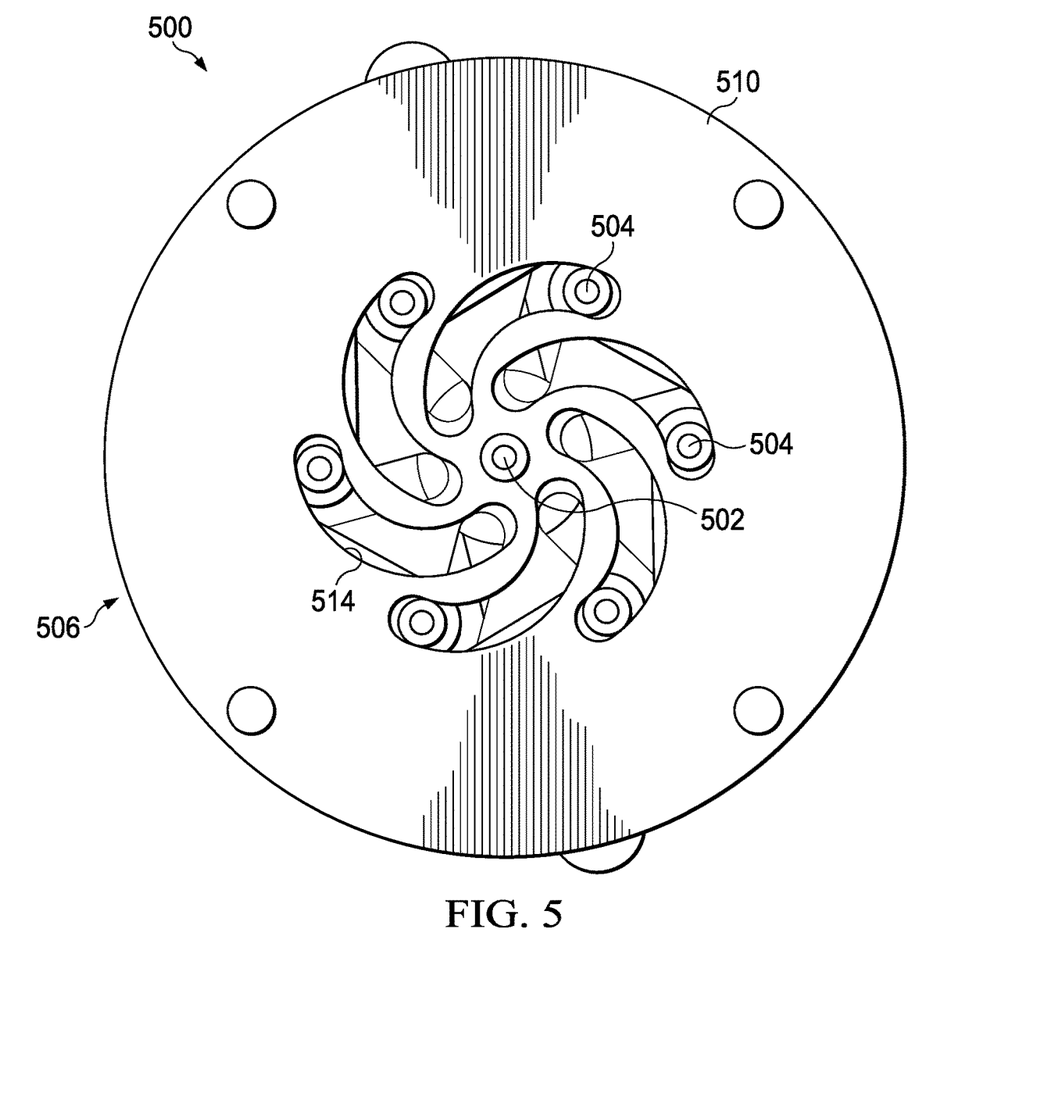
Figure 6:
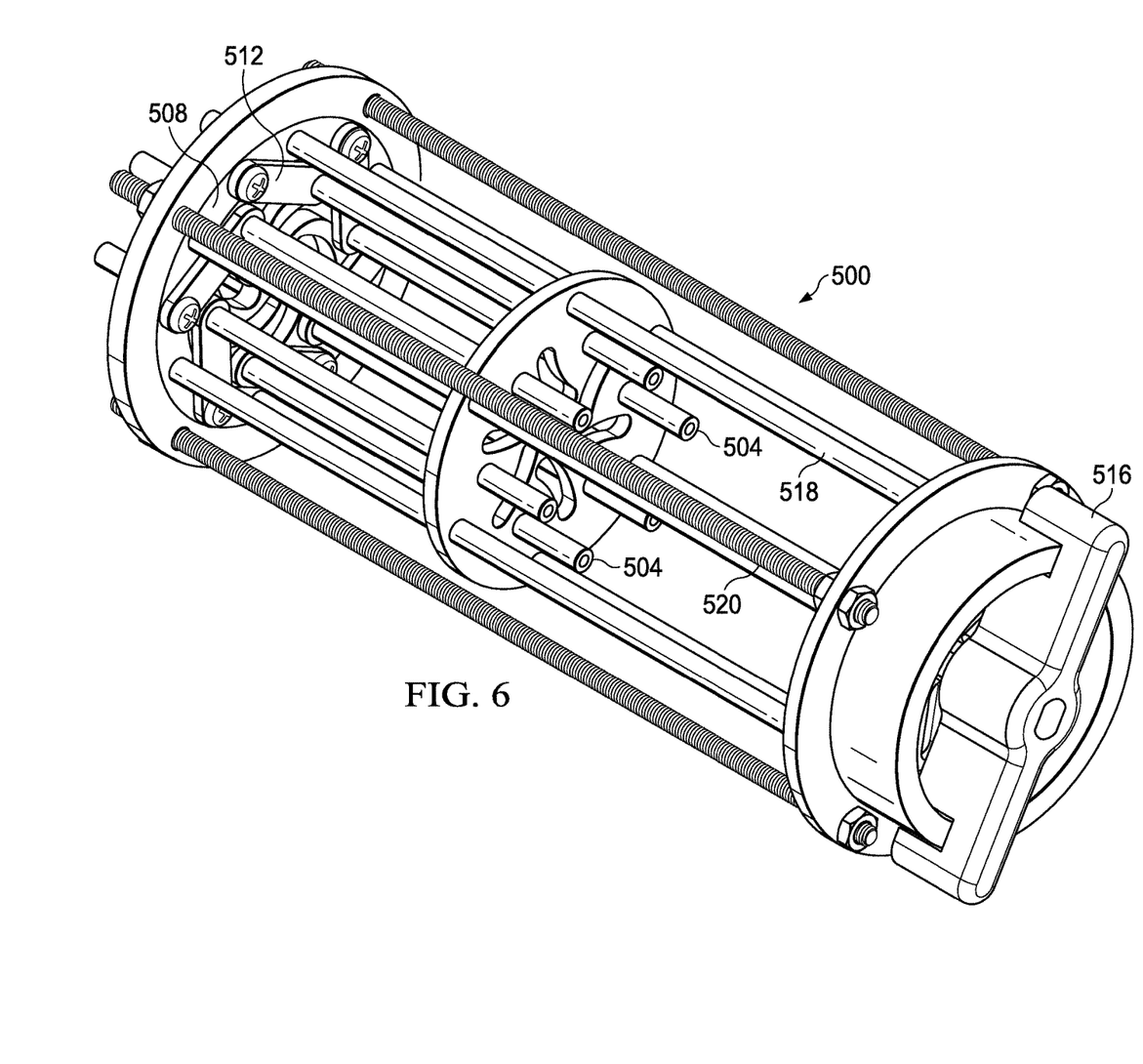
Figure 7:
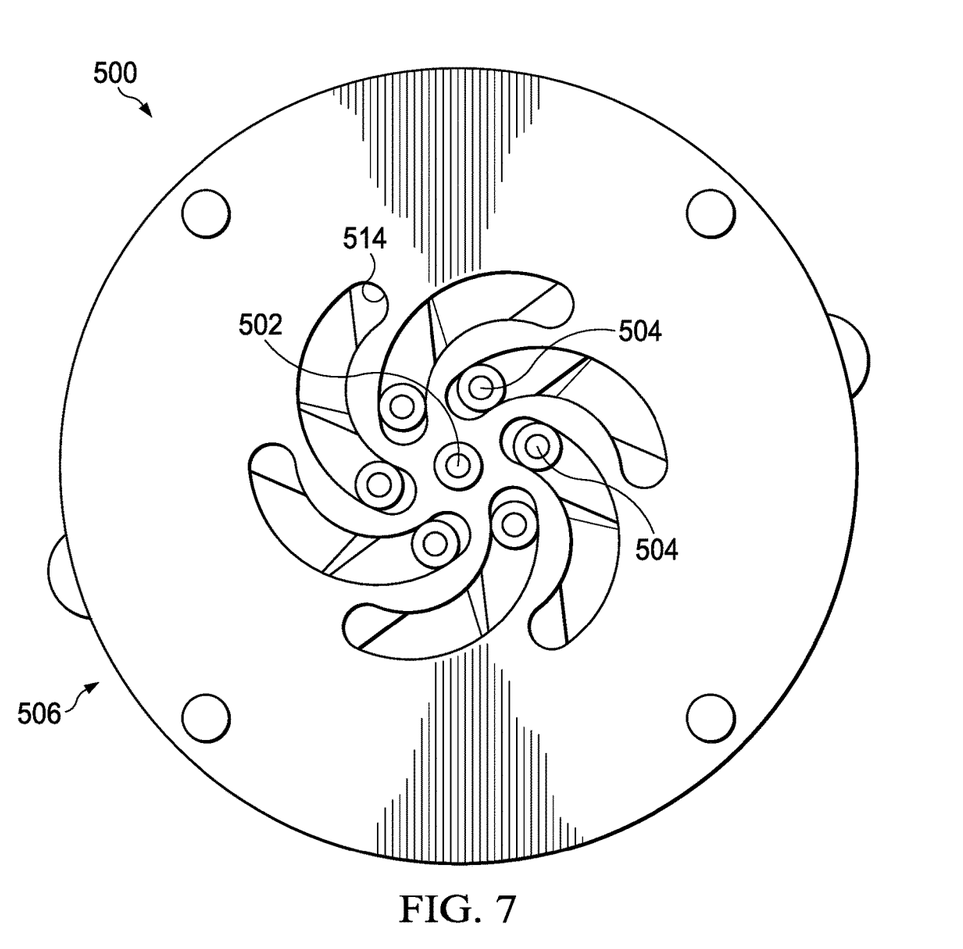
Figure 8:
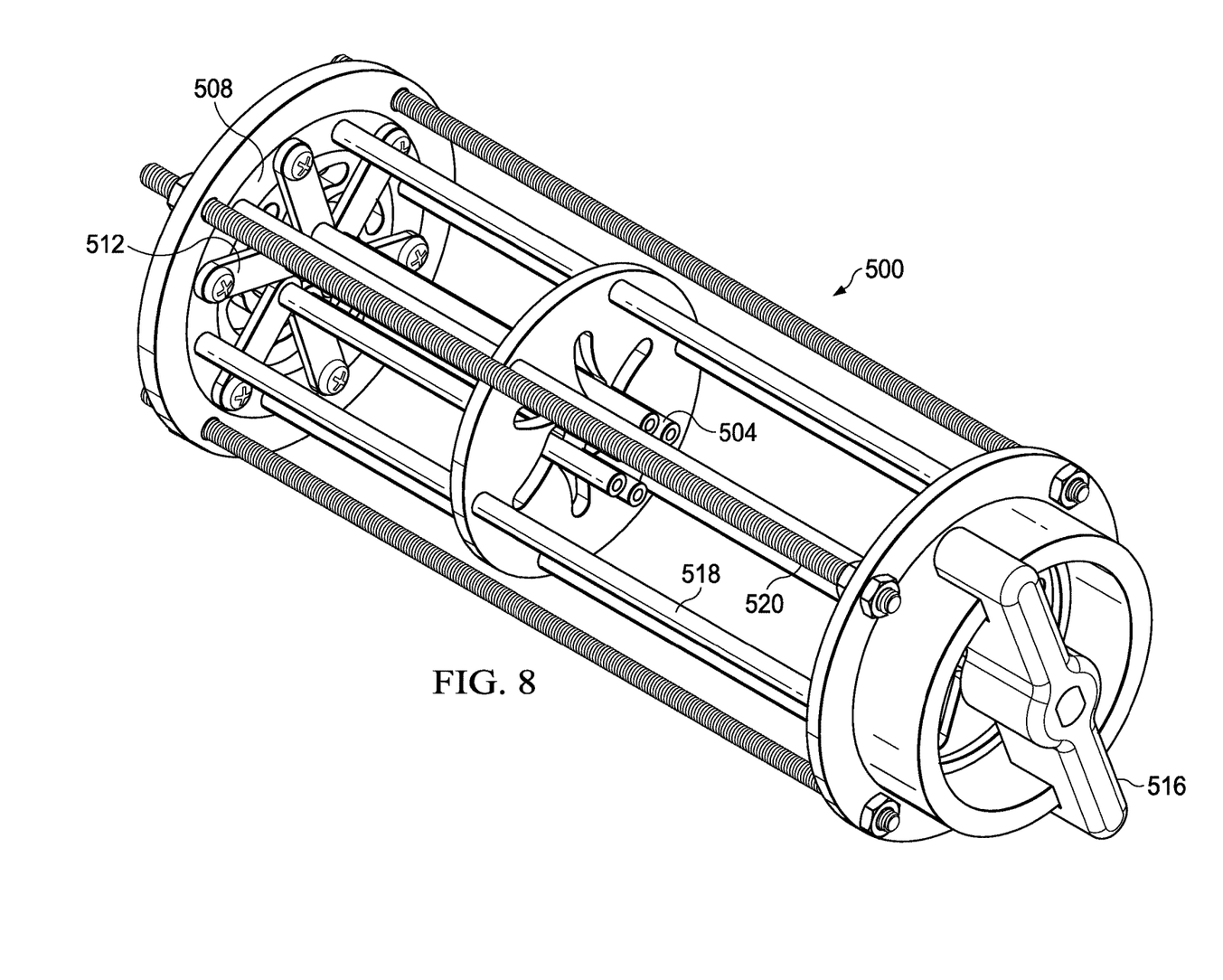
Figure 9:
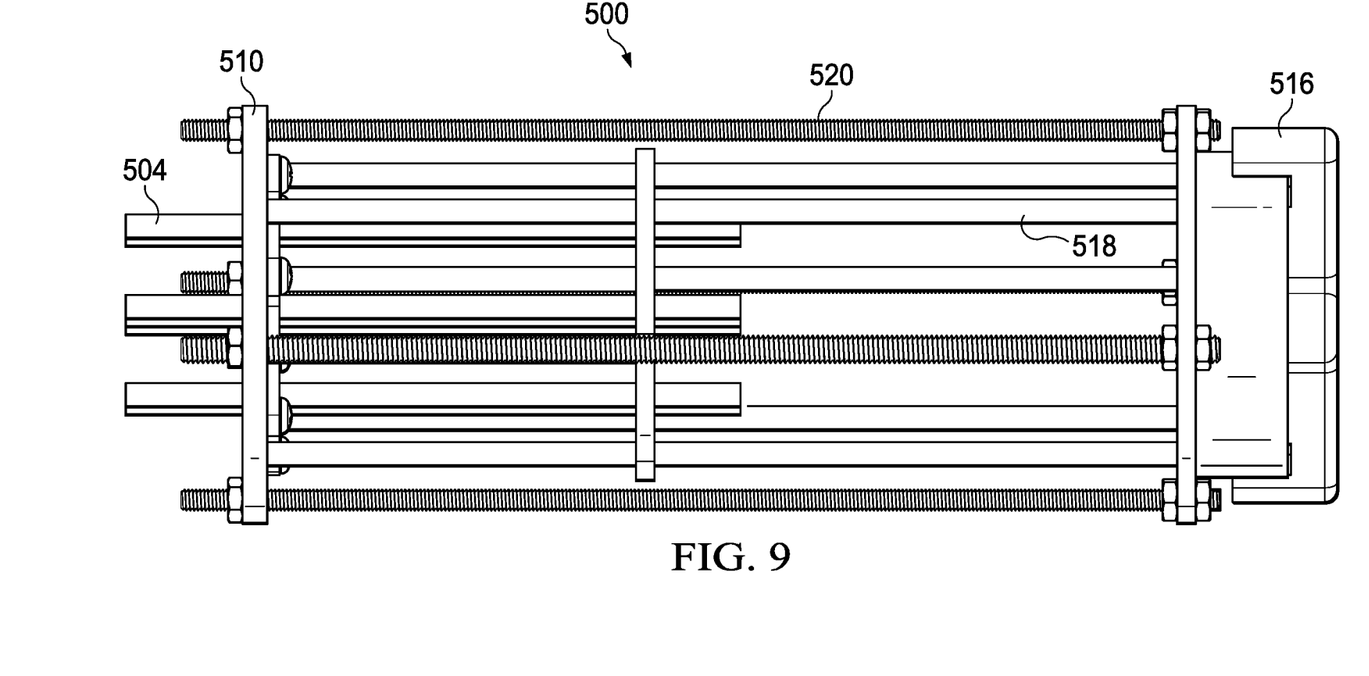
FIGS. 9-10 show views of an embodiment of a fiber optic probe that provides variable distance between excitation and collection fibers in accordance with principles disclosed herein.
Figure 10:
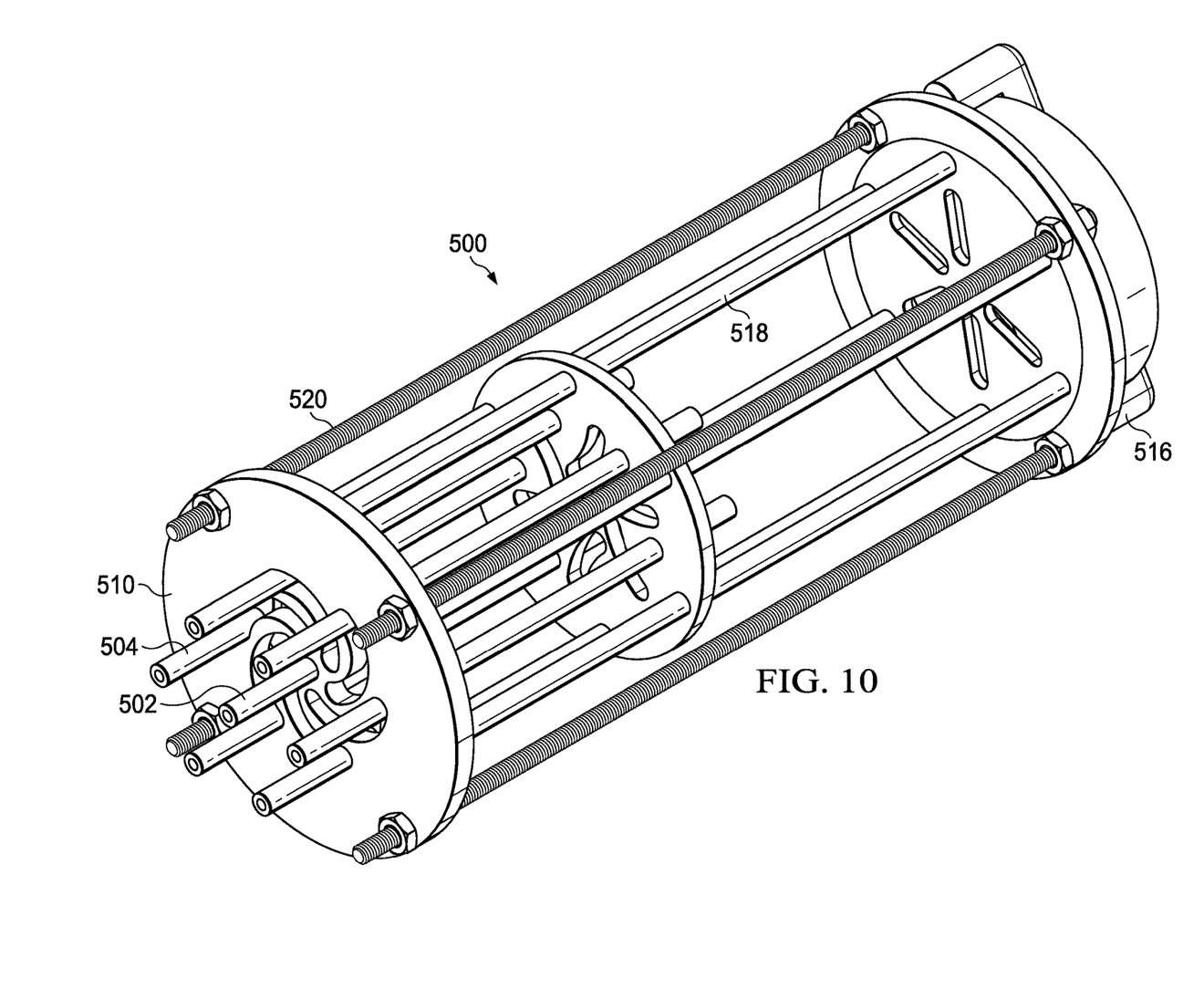

The iris-based fiber probe 500 allows the Δs between the collection fiber tubes 504 and excitation fiber tube 502 to be altered while the probe 500 is in use. The turnkey 516 can be rotated clockwise to move the collection fiber tubes 504 together toward (Close position shown in FIGS. 7 and 8) the excitation tube 502. FIGS. 7 and 8 show the collection fiber tubes 504 moved to a location near the center of the iris 506 (i.e., near the excitation fiber tube 502). The turnkey 504 can be rotated counterclockwise to concurrently move the collection fiber tubes 512 away from (Open position shown in FIGS. 5 and 6) the excitation tube 110. FIGS. 5 and 6 show the collection fiber tubes 504 moved to a location farther away from the center of the iris 506 (i.e., farther from the excitation fiber tube 502). The movements of collection fiber tubes 504 are mechanically synchronized to maintain identical Δs at all times, which means the collection fiber tubes 504 are located on a circle of the same diameter at all times.

Figure 11:
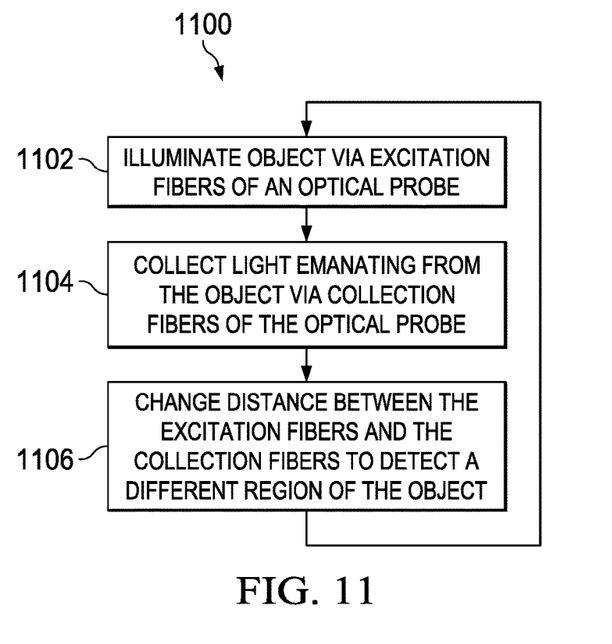
FIG. 11 shows a flow diagram for a method for optical spectroscopy and imaging using a fiber optic probe that provides variable distance between excitation and collection fibers in accordance with principles disclosed herein.

FIG. 11 shows a flow diagram for a method for optical spectroscopy and imaging using a fiber optic probe that provides variable distance between excitation and collection fibers in accordance with principles disclosed herein. Though depicted sequentially as a matter of convenience, at least some of the actions shown can be performed in a different order and/or performed in parallel. Additionally, some embodiments may perform only some of the actions shown.

In block 1102, an optical source, such as a laser, is activated and light generated by the optical source is propagated to an object to be detected by excitation optical fibers 502. Light generated by the optical source illuminates and penetrates the surface of the object.

In block 1104, light emitted from the object is collected by the collection optical fibers 504. The region of the object from which the emitted light is collected is a function of the distance between the excitation optical fibers 502 and the collection optical fibers 504. The collected light is detected by optical receivers, digitized, and provided to an optical data processing system for processing of object data, rendering of optical spectra or an image of the object, detection of features of the object, etc.

In block 1106, distance separating the excitation optical fibers 502 and the collection optical fibers 504 is changed to allow optical spectroscopy and imaging of a different region (e.g., a different depth) of the object. The distance between the excitation optical fibers 502 and the collection optical fibers 504 may be changed by opening or closing an iris structure 506 that moves the collection optical fibers 504 relative to the excitation optical fibers 502. Optical spectroscopy and imaging of the different region of the object continues in block 1102.

Figure 12:
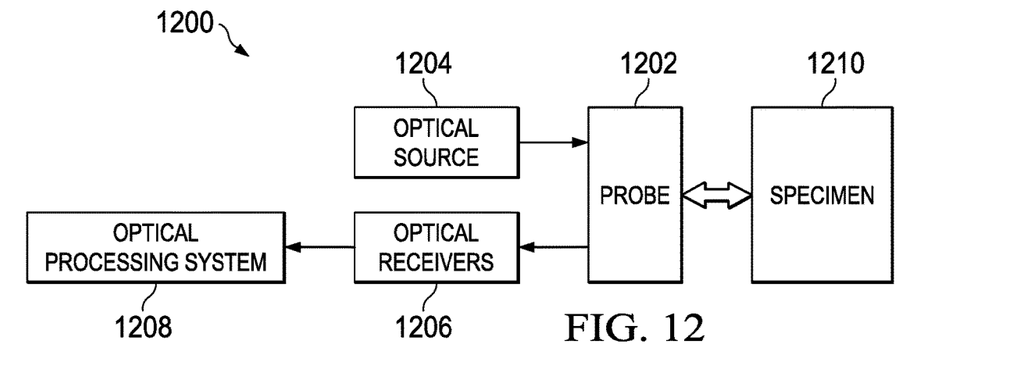
FIG. 12 shows a block diagram of an optical spectroscopy and imaging system using a fiber optic probe that provides variable distance between excitation and collection fibers in accordance with principles disclosed herein.

FIG. 12 shows a block diagram of an optical spectroscopy and imaging system 1200 that includes a fiber optic probe that provides variable distance between excitation and collection fibers in accordance with principles disclosed herein. The system 1200 includes an optical source 1204 (or multiple optical sources), one or more optical receivers 1206, an optical data processing system 1208, and an optical probe 1202. The optical probe 1202 may be optical probe 100, 200, 300, 400, or 500 disclosed herein. Accordingly, the optical probe 1202 includes one or more excitation fibers, one or more collection fibers, and a mechanism to vary the distance between the excitation fibers and the collection fibers. During operation of the system 1200, the distance separating the collection fibers and the excitation fibers in the probe 1202 may be changed to provide optical spectroscopy and imaging at different depths within the specimen 1210 as disclosed herein.

The optical source 602 may be a near-infrared laser or any other light source suitable for illumination of the specimen 1210 in the context of optical spectroscopy and imaging. Light generated by the optical source 1204 is conducted to the excitation fibers of the optical probe 1202, and provided from the excitation fibers to illuminate the specimen 1210. Light emitted by the specimen responsive to the illumination is gathered by the collection fibers in the optical probe 1202, and conducted to the optical receivers 1206.

The optical receivers 1206 are photodetectors that detect light emitted by the specimen 1210. Light detected by the optical receivers 1206 may be converted to electrical signals by the optical receivers 1206 and digitized (in the optical receivers or elsewhere in the system 1200) for processing by the optical data processing system 1208.

The optical data processing system 1208 receives digitized optical signals emitted from the specimen 1210 and processes the signals to provide optical spectroscopy and imaging, detection of structures, etc. of regions within the specimen 1210. The optical data processing system 1208 may include a processor and a storage device for storing software instructions that are executed by the processor. A suitable processor for use in the optical data processing system 1208 may be a general-purpose microprocessor, a digital signal processor, a microcontroller, or other device capable of executing instructions retrieved from a computer-readable storage device. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems.

Instruction and data storage in the data processing system 1208 is coupled to the processor. The storage is a computer readable storage device and may include volatile storage such as random access memory, non-volatile storage (e.g., a hard drive, an optical storage device (e.g., CD or DVD), FLASH storage, read-only-memory), or combinations thereof. Instructions stored in the computer readable medium are retrieved and executed by the processor to process optical data.

Figure 13:
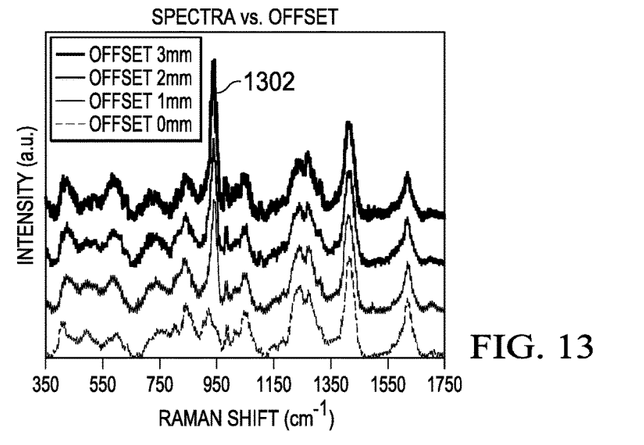
FIGS. 13-18 show results of spatially offset Raman spectroscopy (SORS) applied to in vivo imaging of bone using a fiber optic probe and imaging system in accordance with principles disclosed herein.
Figure 14:
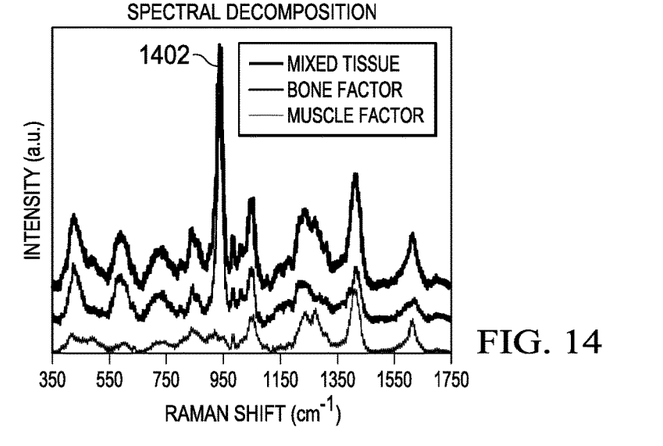
Figure 15:
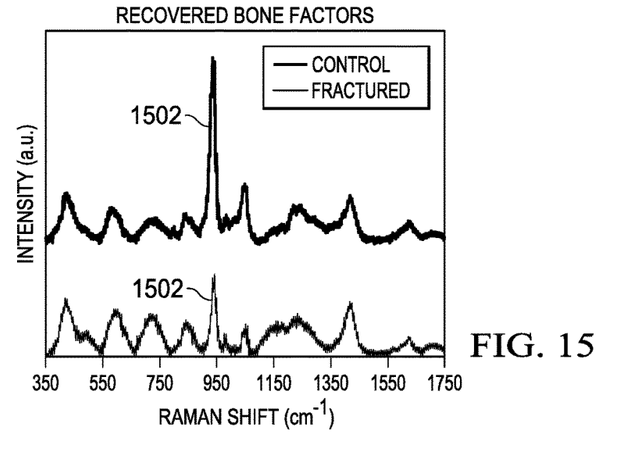

FIGS. 13-18 show results of SORS applied to in-vivo bone imaging using a fiber optic probe and imaging system in accordance with principles disclosed herein. More specifically, FIGS. 13-18 show results of SORS imaging of a healing fractured bone, where the optical probe 1202 is used to collect data from various depths by changing the distance between the illumination optical fiber (e.g., fiber 102) and the collection optical fibers (e.g., fibers 106). FIG. 13 shows SORS spectra versus fiber offset for SORS spectra acquired using the optical probe 1202 with illumination to collection fiber offsets ranging from 0 millimeters to 3 millimeters. FIG. 14 shows spectral decomposition of SORS spectra for mixed tissue (i.e., bone and soft tissue), extracted spectral factors of bone, and extracted spectral factors of muscle. FIG. 15 shows recovered bone factors for a control bone and the healing fractured bone. Reference designators 1302, 1402, and 1502 in FIGS. 13-15 identify the spectral characteristics of bone hydroxyapatite in the SORS spectra.

Figure 16:
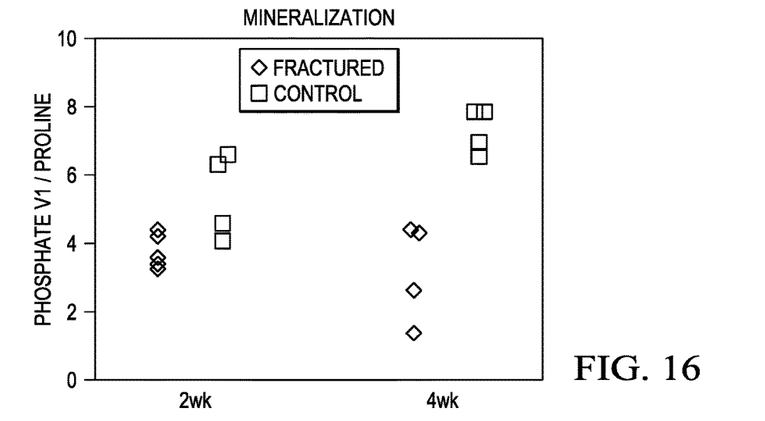
Figure 17:
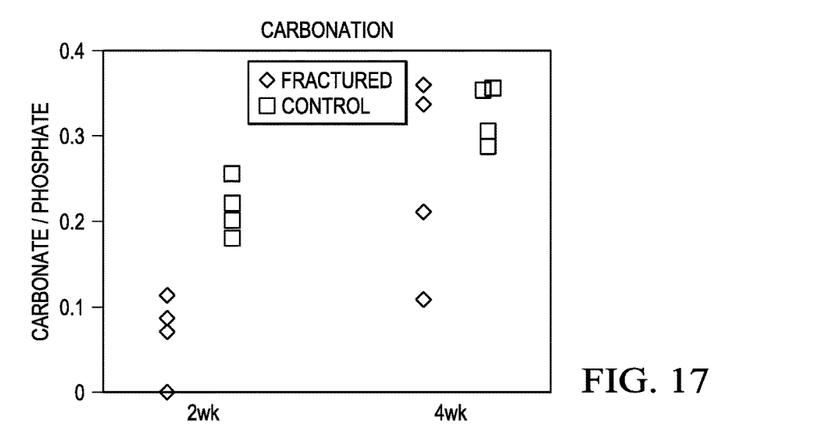
Figure 18:
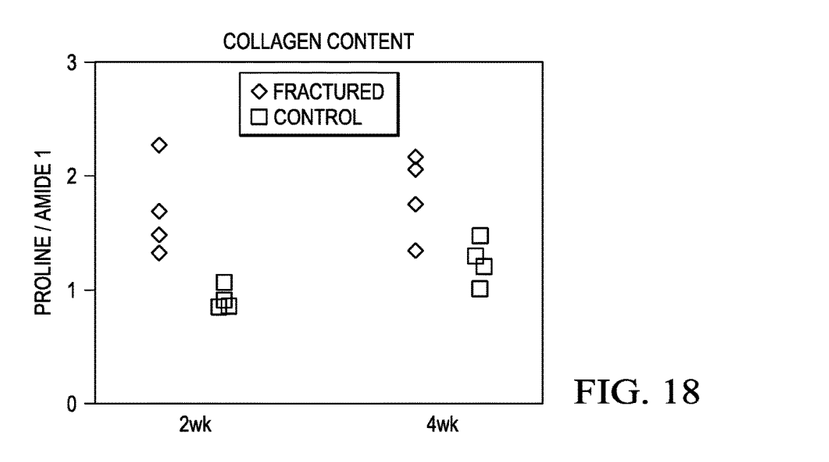

FIGS. 16-18 show compositional parameters (collagen mineralization, carbonation, and collagen content), derived from analysis of bone signals, of the healing fractured bone and control bone at two weeks and four weeks after fracture. At two weeks after fracture, the healing fractured bone demonstrated lower mineral and carbonate level and higher collagen content in the callus than the control bone. At 4 weeks after fracture, the mineralization of the healing fractured bone is still lower than the control bone, but higher than at the 2-week time point. An increase in carbonation is also observed at 4 weeks to an extent that is close to the level of control bone.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An optical probe comprising:
one or more first optical fibers to deliver light to an object;
one or more second optical fibers to collect light emitted from the object; and
one or more actuators configured to change a distance between the first optical fibers and the second optical fibers while the object is being illuminated by light emitted from the first optical fibers, wherein the one or more actuators comprise:
a mechanical iris configured to change a spatial offset between the first optical fibers and the second optical fibers, and the mechanical iris comprises:
an actuating ring;
a base ring; and
one or more blades, wherein a first end of each of the blades is rotatably attached to the actuating ring.

2. The probe of claim 1, wherein one of the first optical fibers or the second optical fibers is disposed along a center line of the probe.

3. The probe of claim 1, wherein:
the actuators are coupled to one of the first optical fibers or the second optical fibers;
the actuators are disposed to form a ring about a center line of the probe; and
movement of the actuators changes a distance between the actuators and the center line of the probe.

4. The probe of claim 1, wherein the base ring comprises:
one or more curved slots, a first end of the curved slots nearer a center line of the probe than a second end of the curved slots;
wherein a second end of each of the blades is coupled to one of the first optical fibers or the second optical fibers and the second end of each of the blades is moveable along one of the curved slots of the base ring.

5. The probe of claim 4, wherein rotation of the actuating ring causes each of the blades to move along one of the curved slots of the base ring to change the distance between the first optical fibers and the second optical fibers.

6. The probe of claim 1, wherein a second end of each of the blades is rotatably attached to the base ring; wherein each of the blades comprises a first arcuate section and a second arcuate section and each of the blades is coupled to one of the first optical fibers or the second optical fibers at an intersection of the first arcuate section and the second arcuate section.

7. The probe of claim 6, wherein rotation of the actuating ring causes the intersection of the first arcuate section and the second arcuate section of each of the blades to move along a curved path and change the distance between the first optical fibers and the second optical fibers.

8. An optical probe comprising:
a first optical fiber to deliver light to an object;
a plurality of optical fibers to collect light emitted from the object; and
a plurality of actuators configured to change a distance between the first optical fiber and the plurality of optical fibers while the object is being illuminated by light emitted from the first optical fiber;
wherein the first optical fiber is disposed along a center line of the probe;
wherein the actuators are coupled to the plurality of optical fibers and disposed to form a ring about the center line of the probe; and movement of the actuators changes a distance between the actuators and the center line of the probe, wherein the actuators comprise a mechanical iris that operates to change a spatial offset between the first optical fiber and the plurality of optical fibers, and the mechanical iris comprises:

an actuating ring;
a base ring; and
one or more blades, wherein a first end of each of the blades is rotatably attached to the actuating ring.

9. The probe of claim 8:
wherein the base ring comprises one or more curved slots, a first end of the curved slots nearer the center line of the probe than a second end of the curved slots;
wherein a second end of each of the blades is coupled to one of the plurality of optical fibers and the second end of each of the blades is moveable along one of the curved slots of the base ring; and
wherein rotation of the actuating ring causes each of the blades to move along one of the curved slots of the base ring to change the distance between the first optical fiber and the plurality of optical fibers.

10. The probe of claim 8:
wherein a second end of each of the blades is rotatable attached to the base ring;
wherein each of the blades comprises a first arcuate section and a second arcuate section and each of the blades is coupled to one of the plurality of optical fibers at an intersection of the first arcuate section and the second arcuate section;
wherein rotation of the actuating ring causes the intersection of the first arcuate section and the second arcuate section of each of the blades to move along a curved path that changes the distance between the first optical fiber and the plurality of optical fibers.

* * * * *